US006989071B2

(12) United States Patent
Kocur et al.

(10) Patent No.: US 6,989,071 B2
(45) Date of Patent: *Jan. 24, 2006

(54) STENT WITH CHANNEL(S) FOR CONTAINING AND DELIVERING BIOLOGICALLY ACTIVE MATERIAL AND METHOD FOR MANUFACTURING THE SAME

(75) Inventors: Gordon John Kocur, Lino Lakes, MN (US); Timothy Samuel Girton, N Maple Grove, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 179 days.

This patent is subject to a terminal disclaimer.

(21) Appl. No.: 10/633,864

(22) Filed: Aug. 4, 2003

(65) Prior Publication Data

US 2004/0030218 A1    Feb. 12, 2004

Related U.S. Application Data

(63) Continuation of application No. 09/774,218, filed on Jan. 30, 2001, now Pat. No. 6,752,829.

(51) Int. Cl.
*B32B 31/00* (2006.01)
*A61F 2/00* (2006.01)

(52) U.S. Cl. ............. 156/293; 156/294; 606/108; 623/1.15; 623/1.42

(58) Field of Classification Search ............... 156/293, 156/294; 606/108; 623/1.15, 1.42
See application file for complete search history.

(56) References Cited

U.S. PATENT DOCUMENTS 4,655,771 A    4/1987    Wallsten

| 4,733,665 A | 3/1988 | Palmaz |
| 4,800,882 A | 1/1989 | Gianturco |
| 4,886,062 A | 12/1989 | Wiktor |
| 4,954,126 A | 9/1990 | Wallsten |
| 5,061,275 A | 10/1991 | Wallsten et al. |
| 5,098,381 A | 3/1992 | Schneider |
| 5,254,089 A | 10/1993 | Wang |
| 5,389,314 A | 2/1995 | Wang |
| 5,409,012 A | 4/1995 | Sahatjian |
| 5,411,550 A | 5/1995 | Herweck et al. |

(Continued)

FOREIGN PATENT DOCUMENTS

WO    WO 99/17682    4/1999

(Continued)

OTHER PUBLICATIONS

International Search Report as to PCT/US02/02635 which claims priority based on U.S. Appl. No. 09/774,218.

*Primary Examiner*—Jeff H. Aftergut
*Assistant Examiner*—Justin Fischer
(74) *Attorney, Agent, or Firm*—Jones Day

(57) ABSTRACT

The invention is directed to an implantable stent prosthesis comprising a sidewall and at least one channel for containing a biologically active material. A method for making such stent prosthesis is also disclosed. In the method, at least one tube or mandrel is placed in contact with a covering material on a stent and surrounded by the covering material to form a channel. Alternatively, a channel can be formed by covering the tube or mandrel with a channel material and exposing the covered tube or mandrel to an appropriate treatment. The channel can be attached to a sidewall of a stent or attached to a strut material to form a stent wire. A method of treating an afflicted area of a body lumen by implanting the stent prosthesis is also disclosed.

14 Claims, 5 Drawing Sheets

U.S. PATENT DOCUMENTS

| | | |
|---|---|---|
| 5,486,191 A | 1/1996 | Pasricha et al. |
| 5,603,694 A | 2/1997 | Brown et al. |
| 5,735,892 A | 4/1998 | Myers et al. |
| 5,755,722 A | 5/1998 | Barry et al. |
| 5,769,883 A | 6/1998 | Buscemi et al. |
| 5,810,767 A | 9/1998 | Klein |
| 5,824,046 A | 10/1998 | Smith et al. |
| 5,843,033 A | 12/1998 | Ropiak |
| 5,843,172 A | 12/1998 | Yan |
| 5,857,998 A | 1/1999 | Barry |
| 5,891,108 A | 4/1999 | Leone et al. |
| 5,928,247 A | 7/1999 | Barry et al. |
| 5,954,693 A | 9/1999 | Barry |
| 5,981,568 A | 11/1999 | Kunz et al. |
| 5,997,468 A | 12/1999 | Wolff et al. |
| 6,004,348 A * | 12/1999 | Banas et al. ............... 623/23.7 |
| 6,071,305 A | 6/2000 | Brown et al. |
| 6,096,070 A | 8/2000 | Ragheb et al. |
| 6,124,523 A | 9/2000 | Banas et al. |
| 6,139,573 A * | 10/2000 | Sogard et al. ............. 623/1.13 |
| 6,273,908 B1 | 8/2001 | Ndondo-Lay |
| 6,273,913 B1 | 8/2001 | Wright et al. |
| 6,287,628 B1 | 9/2001 | Hossainy et al. |
| 6,379,382 B1 | 4/2002 | Yang |
| 6,395,326 B1 | 5/2002 | Castro et al. |
| 6,491,666 B1 | 12/2002 | Santini, Jr. et al. |
| 6,558,422 B1 | 5/2003 | Baker et al. |
| 6,638,302 B1 | 10/2003 | Curcio et al. |
| 6,709,379 B1 | 3/2004 | Brandau et al. |
| 6,752,829 B2 | 6/2004 | Kocur et al. |
| 6,793,672 B2 * | 9/2004 | Khosravi et al. .......... 623/1.13 |
| 2001/0010012 A1 | 7/2001 | Edwin et al. |
| 2002/0038146 A1 | 3/2002 | Harry |

FOREIGN PATENT DOCUMENTS

| | | |
|---|---|---|
| WO | WO 01/67991 | 9/2001 |
| WO | WO 01/87372 | 11/2001 |

* cited by examiner

STENT WITH CHANNEL(S) FOR CONTAINING AND DELIVERING BIOLOGICALLY ACTIVE MATERIAL AND METHOD FOR MANUFACTURING THE SAME

This application is a continuation of U.S. application Ser. No. 09/774,218, filed Jan. 30, 2001.

FIELD OF THE INVENTION

This invention relates generally to an implantable medical device for delivering biologically active materials. More specifically, the invention relates to an implantable stent prosthesis for delivering a biologically active material and a method for manufacturing the same. More particularly, the invention is directed to a stent having one or more channels for containing and delivering a biologically active material.

BACKGROUND OF THE INVENTION

Balloon angioplasty has been very effective in treating stenosis, i.e., to open blocked vessels and restore normal levels of blood flow. However, although once a blocked vessel is opened, the treated vessel has a tendency to restenose, i.e., reclose, shortly after the procedure. Thus, patients have to repeatedly be treated with angioplasty or surgery.

Implantable stent prosthesis or stents are used to reduce restenosis after balloon angioplasty or other procedures using catheters. A stent in the form of a wire mesh tube props open an artery that has recently been cleared using angioplasty. The stent is collapsed to a small diameter, placed over an angioplasty balloon catheter and moved into the area of the blockage. When the balloon is inflated, the stent expands, locks in place and forms a scaffold to hold the artery open. Usually, the stent stays in the artery permanently, holds it open, improves blood flow to the heart muscle and relieves symptoms. The stent procedure is fairly common, and various types of stents have been developed and actually used.

However, the metal surfaces of stents currently in use may trigger restenosis. To prevent the stented arteries from reclosing, patients who receive stents must take one or more anticoagulating drugs, such as heparin, aspirin, coumadin, dextran, and/or persantine even though systemic application of anticoagulants has been known to cause bleeding complications.

To reduce the likelihood of restenosis caused by the metal surface of such stents, stents covered with polymers and a drug have been offered. However, those covered stents are still not completely satisfactory. Therefore, there is a need for additional devices or methods to reduce the necessity for systemic application of anticoagulants and alleviate restenosis.

Further, for certain diseases which are localized to a particular part of body, the systemic administration of a biologically active material for the treatment of these diseases may not be preferred because of the inefficiencies associated with the indirect delivery of the biologically active material to the afflicted area. Therefore, there is a need for a device or method to deliver the biologically active material directly to a particular part of the body.

SUMMARY OF THE INVENTION

These and other objects are accomplished by the present invention. To achieve the aforementioned objectives, we have invented an implantable stent prosthesis with channels and methods for manufacturing the same.

The implantable stent prosthesis of the present invention comprises a sidewall and at least one channel for containing a biologically active material, wherein the sidewall comprises at least in part a plurality of struts having an exterior surface.

The present invention also includes a method for making such implantable stent prosthesis. In an embodiment, at least one tube or mandrel is placed in contact with a covering material on a stent. The tube or mandrel is surrounded by the covering material, and then a channel is formed so that it is located within the covering material and wherein the channel has two open ends.

In another embodiment, a tube or mandrel is covered with a channel material. The covered tube or mandrel is exposed to either heat treatment, chemical treatment or treatment with an adhesive, to form a channel having two open ends. The channel is attached to a sidewall of a stent.

Further, in another embodiment, a tube or mandrel is covered with a channel material. The covered tube or mandrel is exposed to either heat treatment, chemical treatment or treatment with an adhesive, to form a channel having two open ends. The channel is attached to a strut material to form a stent wire. The stent wire is woven to form the sidewall of the stent.

The present invention also includes a method of treating an afflicted area of a surface of a body lumen by implanting the stent prosthesis containing a biologically active material. The biologically active material is delivered to the afflicted area.

DESCRIPTION OF THE DRAWINGS

FIG. 1A shows a cross-sectional view of such an embodiment. In the embodiment, an end of the outer (first) cover is folded to form the channel, i.e., the channel is formed between two layers of covering material. FIG. 1B depicts a cross-sectional view of another embodiment of the invention where a middle portion of the outer stent covering is used to form the channel wall. FIG. 1C depicts a cross-sectional view of an embodiment of the invention where an inner (second) covering is used to form the channel wall. FIG. 1D depicts a cross-sectional view of an embodiment of the invention which is similar to that of FIG. 1B. In FIG. 1B, the channel wall is formed by the outer cover in its entirety. On the other hand, the channel wall in FIG. 1D is formed by the outer cover in part and by the stent sidewall in part.

DESCRIPTION OF THE PREFERRED EMBODIMENTS

Figure 1A:
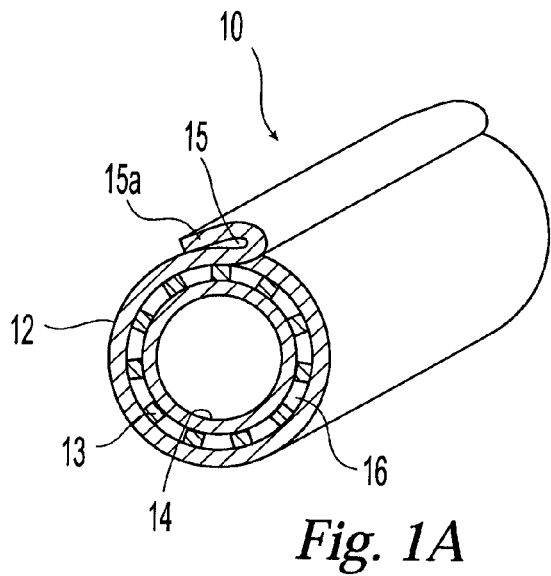
FIGS. 1A, 1B, 1C and 1D show embodiments of a stent with channel for containing a biologically active material where the stent covering material forms the channel wall defining the channel.

An embodiment of the present invention is illustrated in FIG. 1A. FIG. 1A shows a stent 10 having a sidewall 16, made up of a plurality of struts 13. In the embodiment, an exterior surface of the stent sidewall 16 is covered with a first stent covering 12, and an interior luminal surface of the stent sidewall 16 is covered with a second stent covering 14. In this embodiment, the channel is formed by folding one end of the first stent covering 12 to form a channel 15. In this case, the channel wall 15a, which encompasses the space in the channel 15, is formed of the covering material. The term "channel" refers to a tube-like pocket along with the channel wall defining such pocket or space, i.e., the channel comprises both the channel wall and the pocket defined by the channel wall. In this embodiment, the channel 15 is positioned along the longitudinal axis of the stent. When the stent is introduced into a body lumen, the channel 15 contains biologically active material, and both ends of the channel 15 are preferably sealed.

The stent 10 may be prepared by the following steps:

(1) A stent is manufactured by a method known in the art and a stent covering 12 is disposed about the exterior surface of the stent sidewall 16.

(2) A tube or tube-like object having the desired diameter or width or shape is placed on top of the exterior surface of the stent covering near the end of the covering. The covering is then folded around or made to surround the tube, so that an end of the tube protrudes from a first end of the channel 15.

(3) The folded cover is treated by heat or chemical treatment or an adhesive or other method known in the art to form a channel 15 having a channel wall 15a made of the covering material. At this point, the second end of the channel 15 can be sealed by heat-fusing or adhesive or other method known in the art.

(4) A biologically active material can be placed into the channel 15 by injection or other appropriate means known to the skilled artisan. Preferably, the biologically active material is placed into the channel 15 at the first end of the channel as the tube is being removed. Then the first end of the channel 15 can also be sealed.

The last step, placement of a biologically active material into the channel, is not necessarily conducted by a manufacturer but can be done by a user of the devices just prior to implantation. Thus, the stent of the present invention includes a stent with a channel, where only one end is sealed or both ends are open, without any biologically active material contained in the channel. The user would then place a biologically active material into the channel, right before insertion of the stent into a body lumen.

A mandrel can be used to form the channel instead of a tube. Preferably, the mandrel is made of a material which is easily dissolvable in a solvent. When the mandrel is soluble in water or an organic solvent, it can be removed from the channel by dipping the channel containing the mandrel and dissolving the mandrel in water or solvent. Also, the mandrel can contain the biologically active material, and in that case there is no need to remove the mandrel from the channel and no need to later fill the channel with a biologically active material. The mandrel can also be made of a material that is insoluble, such as a plastic or metal, and can be removed leaving the open channel.

Figure 1B:
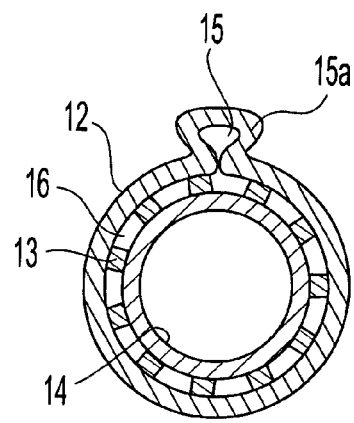
Figure 1C:
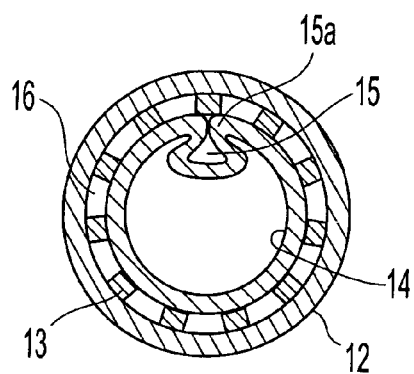
Figure 1D:
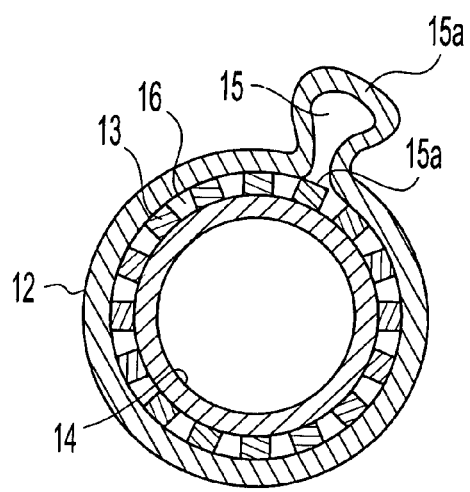

Also the channel 15 need not be positioned near the end of the covering and can be positioned in the middle of the first covering 12 as shown in FIG. 1B. In this case, a tube or mandrel is positioned between the stent sidewall 16 and the first covering 12 as shown in FIG. 1B. Also, as shown in FIG. 1C, the channel 15 can be made from the second, inner, stent covering 14 in the same way as explained above with respect to the first stent covering 12. Moreover, the channel 15 can be formed by the coverings 12, 14 in part and the stent sidewall 16 in part as shown in FIG. 1D.

Figure 2:
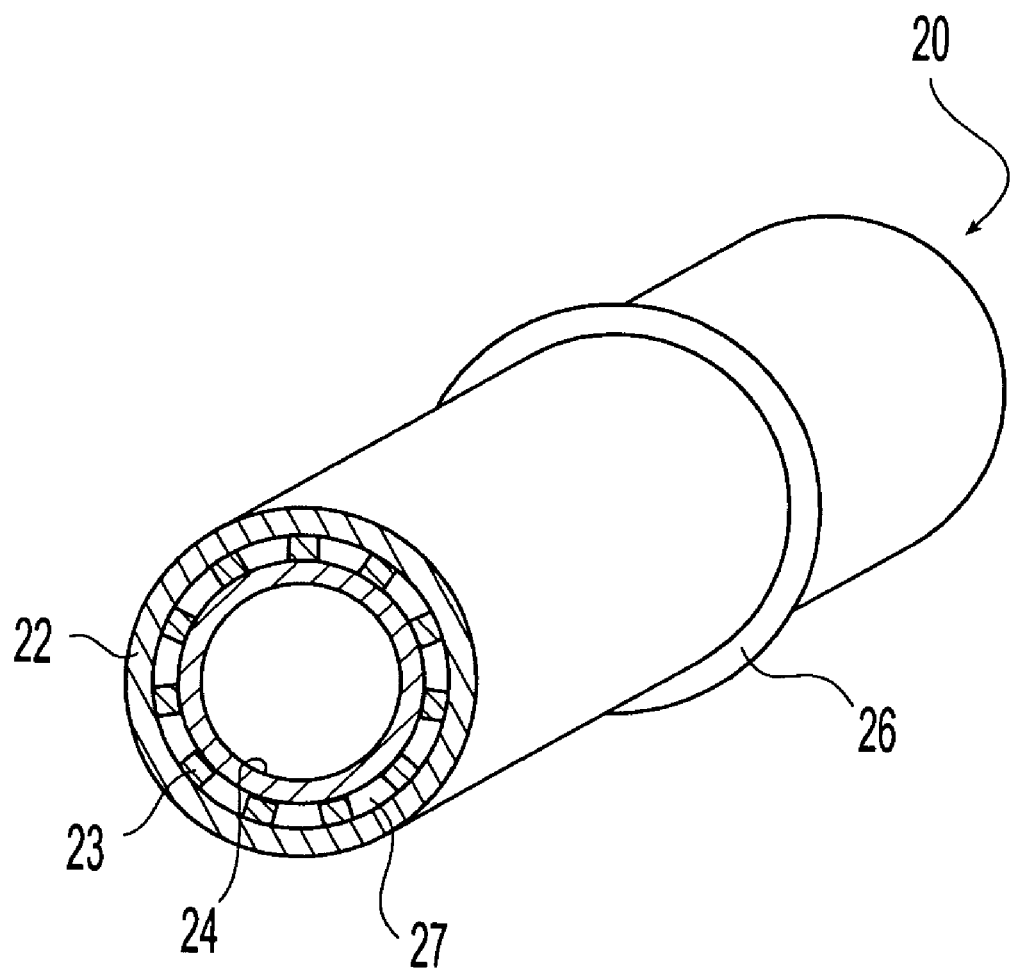
FIG. 2 depicts a perspective view of another embodiment of a stent with a channel positioned along a circumference of the stent.

Another embodiment of the invention is illustrated in FIG. 2. In this embodiment, the channel 26 is positioned along a circumference of the stent 20 having a sidewall 27 comprising a plurality of struts 23. Such channel 26 can be made in the same way as explained above, i.e., by inserting a tube or mandrel between the stent sidewall 27 the first stent covering 22 or between layers of the stent covering and then placing the first stent covering 22 material around the tube or mandrel, to form a channel 26. The covering surrounding the tube or mandrel can be treated by heat, chemical or adhesive to form the channel 26. One end of the tube or mandrel may be left protruding from a first open end of the channel 26 and second open end of the channel 26 is sealed by an appropriate means, such as by heat or chemical treatment or by adhesives. Then, a biologically active material is placed into the channel 26 at the first open end. The tube or mandrel is taken out of the channel 26, and the first end of the channel 26 can be sealed. Likewise, the channel 26 can be positioned about the outer surface or inner luminal surface of the stent sidewall 27 in a spiral-like manner.

In addition, besides being formed of a stent covering material, channels 15, 26 may be formed from a layer of a channel material. First, a channel 15, 26 is prepared by wrapping a tube or mandrel with a layer of channel material, i.e., the channel wall is formed of the channel material. More than one layer can be used. These layers need not be of the same type of material. The types of materials used for the layers can be selected to affect the release rate of the biologically active materials. The channel 15, 26 is positioned in the stent covering material and attached or fused to the covering material by heat or chemical treatment or by using an adhesive. A material used for forming the channel can be the same as or different from the material for the stent coverings 2, 14, 22, 24.

Figure 3A:
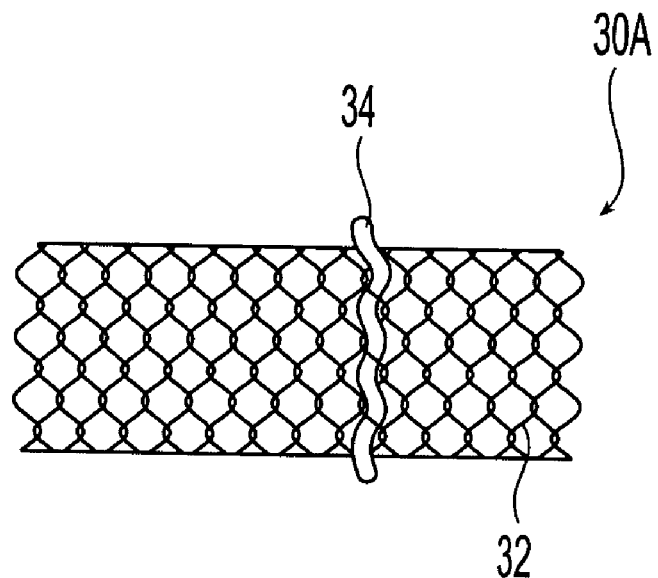
FIGS. 3A and 3B illustrate perspective views of embodiments of a stent of the invention wherein a channel is woven with the struts or wires of a stent.
Figure 3B:
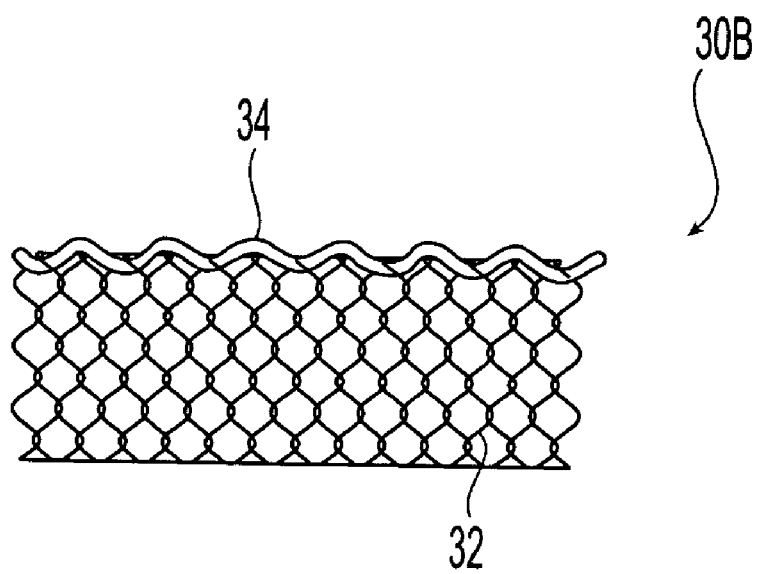

Also, channel 34 made from the channel material can be used to form the stent sidewall. In FIGS. 3A and 3B, the channel 34 is produced separately, and then woven with the struts 32 to form the stent sidewall. Alternatively, the channel 34 can be woven into a prefabricated stent 30A, 30B comprising struts 32. In FIG. 3A, the channel 34 is woven into the stent 30A along the stents longitudinal axis. In FIG. 3B, the channel 34 is woven into the stent 30B along a circumference of the stent 30B. The channel 34 can also be woven in other configurations, such as in a spiral manner. These stents having sidewalls comprising channels woven with the stent struts can be covered with a covering material (not shown). The biologically active material can be placed into the channel before or after the channel is woven into the stent.

Figure 4A:
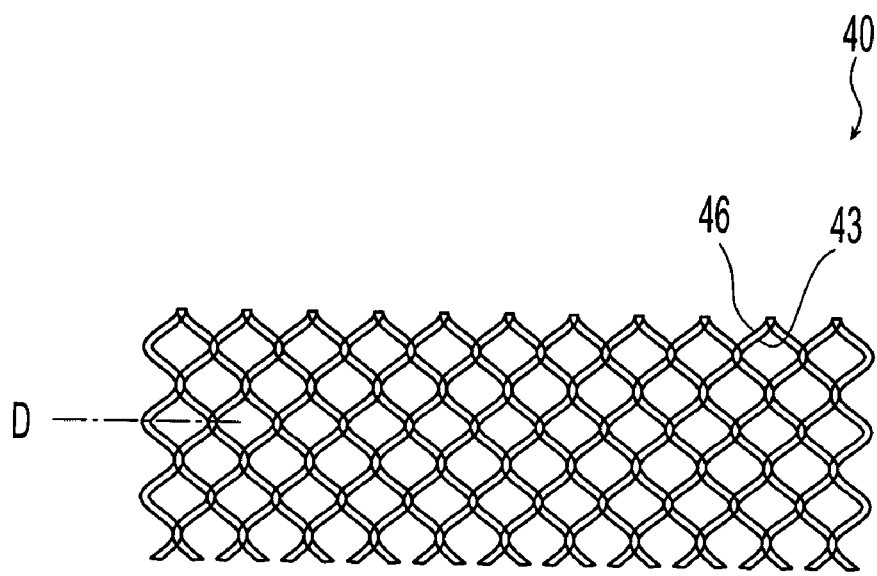
FIG. 4A illustrates a stent wherein a channel is fused to the stent struts.
Figure 4B:
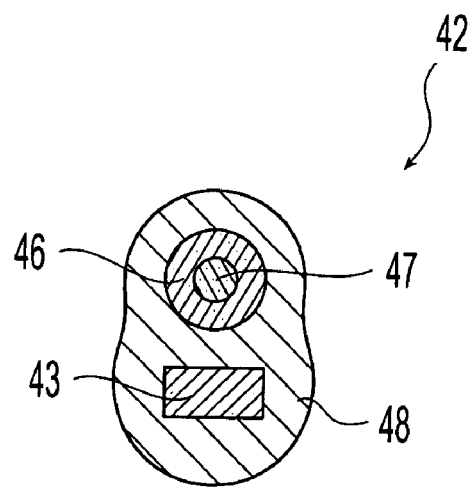
FIG. 4B is a cross-sectional view at the line D in FIG. 4A of the stent strut and the channel.

FIG. 4A illustrates another embodiment of the invention wherein a piece stent strut material 43 and a channel 46 are combined or fused together to form a stent wire 42. These wires are used to form the sidewall of the stent 40. The stent may also be coated with a covering material (not shown in FIG. 4A). FIG. 4B shows a cross-sectional view of such a stent wire 42 comprising strut material 43 and a channel 46 coated together with a covering material 48. Either the entire stent sidewall or a part thereof can be made up of such stent wires 42. The covering material may be placed over the strut material 43 and channel 46 before or after they are used to make the stent sidewall.

One of the methods for producing the stent 40 comprises the following steps: forming a channel 46 by wrapping a tube or mandrel 47 with a channel wall material and fusing the channel 46 to the strut material 43. The channel 46 and strut material are coated with a covering material 48. As the tube or mandrel 47 is removed, a biologically active material is placed into the channel 46 and both ends of the channel can be sealed by an appropriate means, such as with chemical treatment or by heat. The coated stent wire 42 is woven into the stent 40. The order of the steps is totally interchangeable. For example, the coating step is not necessarily before the weaving step. Also, the step of placing the biologically active material can be done after the weaving step. The biologically active material can be introduced into the channel by diffusion in a solution/vapor or migration. Also, in another embodiment, a channel made of a channel material can be fused to the struts of a prefabricated stent.

Figure 5:
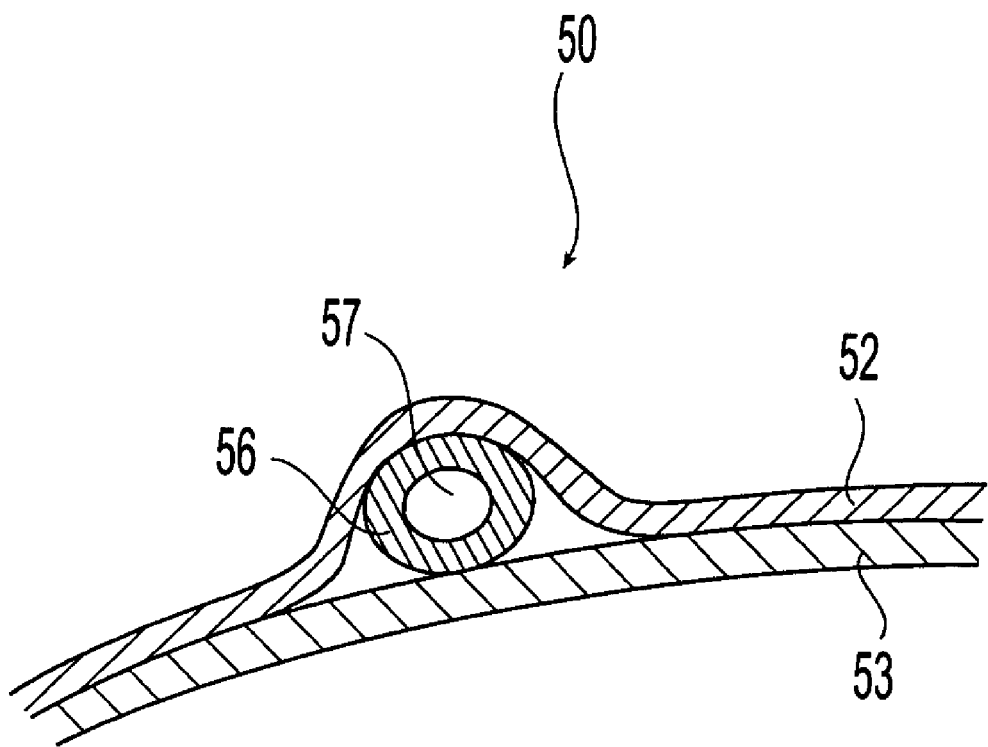
FIG. 5 depicts a cross sectional view of a channel and positioned between two layers of a stent covering.

In FIG. 5, a channel 57 is inserted between two layers 52 and 53 of a stent covering material. The channel 56 containing a tube or mandrel 57 may be separately prepared from a layer of channel material and inserted into the two covers 52 and 53 which are covering a stent. Alternatively, a stent cover 50 wherein two cover layers 52 and 53 are sandwiching a channel 56 is formed first, and then the cover 50 may be placed onto a stent.

If the material for the channel cannot withstand the heat or other treatment used for processing the stent covering, the channel may be formed separately from a channel material and then inserted into another channel which is formed with the stent covering material as explained above.

In another embodiment of the present invention, the tent-like space formed between (a) stent cover layer(s) and a stent strut can be used as a channel for containing a biologically active material. The tent-like space can be enlarged by inserting a tube of desired diameter into it.

A stent can have more than one channel. Each channel can be made of an identical material or different materials and also by an identical method or different methods.

The following is a more detailed description of suitable materials and method useful in producing a stent with channel(s) of the invention.

The term "biologically active material" encompasses therapeutic agents, such as drugs, and also genetic materials and biological materials. The genetic materials mean DNA or RNA, including, without limitation, of DNA/RNA encoding a useful protein stated below, intended to be inserted into a human body including viral vectors and non-viral vectors. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Non-viral vectors include artificial chromosomes and mini-chromosomes, plasmid DNA vectors (e.g., pCOR), cationic polymers (e.g., polyethylene-imine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor α and β, platelet derived endothelial growth factor, platelet derived growth factor, tumor necrosis factor α, hepatocyte growth factor and insulin like growth factor ), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include whole bone marrow, bone marrow derived mono-nuclear cells, progenitor cells (e.g., endothelial progentitor cells) stem cells (e.g., mesenchymal, hematopoietic, neuronal), pluripotent stem cells, fibroblasts, macrophage, and satellite cells.

Biologically active material also includes non-genetic therapeutic agents, such as:
  anti-thrombogenic agents such as heparin, heparin derivatives, urokinase, and PPack (dextrophenylalanine proline arginine chloromethylketone);
  anti-proliferative agents such as enoxaprin, angiopeptin, or monoclonal antibodies capable of blocking smooth muscle cell proliferation, hirudin, and acetylsalicylic acid, amlodipine and doxazosin;
  anti-inflammatory agents such as glucocorticoids, betamethasone, dexamethasone, prednisolone, corticosterone, budesonide, estrogen, sulfasalazine, and mesalamine;
  antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives;
  anesthetic agents such as lidocaine, bupivacaine, and ropivacaine;
  anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;
  vascular cell growth promotors such as growth factors, Vascular Endothelial Growth Factors (FEGF, all types including VEGF-2), growth factor receptors, transcriptional activators, and translational promotors;
  vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;
  cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

A biologically active material can be placed into the channel by various methods including injection as explained above. For instance, after the biologically active material is dissolved or suspended in water or an aqueous solution, it can be injected into the channel. Also, the biologically active material can be introduced into a channel by diffusion in the solution. For example, a stent with an empty channel is dipped in a solution or suspensions of the biologically active material to allow the biologically active material to diffuse into the channel. Also, when the biologically active material is dissolved in an organic solvent, it can be introduced into a channel by diffusion in a vapor of the solvent solution. When the biologically active material is a biological material, such as tissue culture cells, yeast, and bacteria, it can be introduced into a channel by migration or by injection of a culture medium containing the biological material.

Stents suitable for the present invention include any stent for medical purpose without limitation, which are known to the skilled artisan. Stents suitable for the present invention include vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 4,733,665 issued to Palmaz, U.S. Pat. No. 4,800,882 issued to Gianturco and U.S. Pat. No. 4,886,062 issued to Wiktor. Expandable stent may be formed from polymeric, metallic and/or ceramic materials. Suitable materials include, without limitation, metals, such as tantalum, stainless steel, nitinol, titanium, and alloys, and polymeric materials, such as poly-L-lactic acid, polycarbonate, and polyethylene terephtalate. Also, stents made with biostable or bioabsorbable polymers such as poly(ethylene terephthalate), polyacetal, poly(lactic acid), poly(ethylene oxide)/poly(butylene terephthalate) copolymer could be used in the present invention.

Stent covering materials suitable for the present invention include any covering material for the stent which are known to the skilled artisan. The covering can be a polymer, which is preferably selected from elastomeric polymers, e.g., silicones, polyurethanes, thermoplastic elastomers, ethylene vinyl acetate copolymers, polyolefin elastomers, EPDM rubbers, polytetrafluoroethylene (PTFE) or expanded PTFE (ePTFE).

Suitable thickness of the cover are known in the art and can be selected by artisans. The cover can be produced by any method suitable and known in the art. For example, by dipping a stent in a polymer, spraying a polymer covering solution onto a stent, wrapping the stent with a material or encapsulating the stent in a polymer tube.

Examples for suitable materials for making the channel, i.e., channel materials, are, without limitation, poly(L-lactic acid), poly(lactic acid-co-glycotic acid), polyether, polyurethane, and silicone. The material for the channel material can be selected to control release of the drug contained in the channel. For example, in the embodiment where the channel is located in the stent covering, the channel material and covering materials used are selected so that the biologically active material can be released at a certain rate or in a certain manner.

Preferably, the channel has a cylindrical-like shape, where the channel has a circular cross-section as shown in the figures. However, the channel need not be cylindrical. Instead, the channel can have an oblong, square or star-like shaped cross-section, or any other type of shape.

The diameter of the channel of the present invention is not limited and should be selected depending on the type and amount of biologically active material to be deliver, the rate of the delivery, and the method for manufacture. For instance, when the biologically active material is injected into the channel by a syringe rather than by diffusion, migration or by inserting a mandrel containing the biologically active material, the channel diameter should be large enough to allow such injection. When the biologically active material is placed into the channel by migration, the channel should have opening(s), i.e., an open end or pore(s) which are large enough for such migration of the biologically active material into and out of the channel space. Alternatively, the biological material can be trapped in the channel and prevented from migration but allowed to produce a biological active material that can actively regulate biological function. For example, growth-factor producing cells are trapped in the channel, but the growth factor that these cells produce is gradually released from the channel while the cells stay in the channel. Moreover, the present invention may include not only macro channels but also micro channels. The micro channels may be produced by microfabrication, by printing a pattern on the stent or stent cover, or using pre-printed sheets. The macro channels maybe preferable because of their larger capacity for containing biologically active material.

The suitable diameter of the channel depends on various factors, such as the material to be used to make the channel, the manner to inject the biologically active material, the thickness of the material, the size and type of the stent, the configuration of the channel, method of manufacture, amount of the biologically active material to be deliver and the rate of the delivery. The inner diameter of the channel is normally from about 10 $\mu$m to about 1 mm, preferably from about 50 $\mu$m to about 500 $\mu$m.

The thickness of the channel wall is not limited and depends on the biologically active material to be deliver, the rate of the delivery, method for manufacture, and type of channel material used. For example, when the channel material is poly(ethylene terephthalate), the thickness is generally between 10 $\mu$m and 2000 $\mu$m, preferably between 50 $\mu$m and 600 $\mu$m, more preferably 50 $\mu$m and 450 $\mu$m.

The release rate of the biologically active material depends on the degree of porosity of the channel material and covering material, hydrophobicity of the channel material and covering material, the thickness of the channel wall and covering, and the biologically active material's chemical and physical features. Thus, by selecting an appropriate covering material, channel material and a thickness of the covering and/or channel wall, the release rate of a biologically active material can be controlled.

Additionally, a further control can be possible by using wide variety of pharmaceutical forms of the drugs and carriers, such as bars, particles, gels, and fluids.

The release rate of the biologically active material is not necessarily uniform. For example, by selecting a porous material for inner covering of stent and a less porous material for the outer covering, the release rate of the biologically active material at the interior luminal surface of the stent is greater than at the stent's exterior surface. Accordingly, there can be a lag time between the implantation of the stent and the biologically active material is first released. Alternatively, there can be a gradient for a biologically active material contained in the channel. If the concentration of the biologically active material is high in the center of the channel and becomes lower at points further from the center, the release rate can increase with time. If the concentration of the biologically active material is low in the center of the channel and becomes higher as distant from the center, the releasing rate can gradually decrease with time.

In some embodiments, the channel wall has a plurality of ports which allow a biologically active material to pass through. The biologically active material, such as tissue culture cells, yeast, bacteria can migrate through the ports. Such channel may be substantially covered with a covering.

A stent of the present invention can be implanted into a body lumen using any conventional method known in the art. The body lumen into which the stent can be implanted includes blood vessels, urinary tract, coronary vasculature, esophagus, trachea, colon, and biliary tract. Once the stent with the channel(s) is placed in a body lumen, the biologically active material in the channel can be released from the channel by diffusion through the channel wall. In another embodiment of the present invention, a biologically active material is released from the channel by application of pressure. For example, the stent is inserted into a body lumen by a balloon catheter and the biologically active material is squeezed out from the channel when the stent is pressed onto the body lumen surface by expanding balloon.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

We claim:

1. A method for making an implantable stent prosthesis having a sidewall comprised of a plurality of struts and at least one channel comprising a channel wall defining a channel space for containing a biologically active material, the method comprises the steps of:
   (a) covering a tube or mandrel with a channel material;
   (b) forming the channel, having two open ends, by exposing the covered tube or mandrel to a treatment selected from heat treatment, chemical treatment or treatment with an adhesive; and
   (c) attaching the channel to the sidewall.

2. The method of claim 1, wherein the channel is attached to the sidewall by attaching the channel to a strut.

3. The method of claim 2, wherein the channel is attached to the strut by fusing the channel to the strut.

4. The method of claim 2, wherein the channel is attached to the sidewall by weaving the channel with a strut.

5. The method of claim 2, which further comprises covering the channel and strut with a covering material.

6. The method of claim 1, which further comprises removing the tube or mandrel and introducing the biologically active material into the channel.

7. The method of claim 6, wherein the tube or mandrel is removed before the channel is attached to the sidewall.

8. The method of claim 6, wherein the biologically active material is introduced into the channel before the channel is attached to the sidewall.

9. The method of claim 6, wherein the biologically active material is introduced into the channel using a technique selected from injecting the biologically active material into the channel, allowing the biologically active material to diffuse into the channel or allowing the biologically active material to migrate into the channel.

10. The method of claim 1, wherein the channel material is selected from poly(L-lactic acid), poly(lactic acid-co-glycotic acid), polyether, polyurethane, or silicone.

11. A method for making an implantable stent prosthesis having a sidewall comprised of (1) a plurality of struts formed from a strut material and (2) at least one channel comprising a channel wall defining a channel space for containing a biologically active material, the method comprises the steps of:
    (a) covering a tube or mandrel with a channel material;
    (b) forming the channel by exposing the covered tube or mandrel to a treatment selected from heat treatment, chemical treatment, or treatment with an adhesive;
    (c) attaching the channel to strut material to form a stent wire; and
    (d) weaving the stent wire to form the sidewall of the stent.

12. The method of claim 11 wherein the stent wire is covered with a covering material.

13. The method of claim 12 wherein the covering material is selected from silicones, polyurethanes, thermoplastic elastomers, ethylene vinyl acetate copolymers, polyolefin elastomers, EPDM rubbers, polytetrafluoroethylene or expanded polytetrafluoroethylene.

14. The method of claim 12 wherein the stent wire is covered with the covering material before the stent wire is woven.

* * * * *